United States Patent [19]

Ikeda et al.

[11] 3,964,830

[45] June 22, 1976

[54] METHOD FOR INSPECTING FLAWS OF MATERIAL

[75] Inventors: Hiroyuki Ikeda, Yokohama; Takefumi Inagaki, Kawasaki, both of Japan

[73] Assignee: Fujitsu Ltd., Japan

[22] Filed: Mar. 27, 1974

[21] Appl. No.: 455,369

[30] Foreign Application Priority Data
Mar. 30, 1973 Japan.............................. 48-36372

[52] U.S. Cl................................. 356/109; 250/572; 356/237; 356/239
[51] Int. Cl.².............................................. G01B 9/02
[58] Field of Search............ 356/109, 111, 200, 237, 356/239; 250/572, 562, 550

[56] References Cited
UNITED STATES PATENTS

| | | | |
|---|---|---|---|
| 3,518,007 | 6/1970 | Ito.................................. | 356/159 X |
| 3,748,047 | 7/1973 | Millgard et al. ................ | 250/572 X |
| 3,764,216 | 10/1973 | Bliek et al...................... | 356/109 X |

OTHER PUBLICATIONS
Born et al. *Principles of Optics,* Second Ed. Macmillan, pp. 445–449, 1964.

*Primary Examiner*—John K. Corbin
*Assistant Examiner*—Matthew W. Koren
*Attorney, Agent, or Firm*—Maleson, Kimmelman and Ratner

[57] ABSTRACT

A method for inspecting flaws existing on the surface or existing in the inside of material through employment of a coherent and spherical wave of light is disclosed, in which method a flat wave of light, such as He-Ne Laser light, is converted by a lens system into a coherent and spherical wave of the light, and subsequently the spherical wave of the light is brought into impingement upon the material to be inspected and, further, a Fresnel diffraction pattern of the material is produced on an inspection screen through a projection method whereby two-dimensional images, which approximate the shape of the flaws of the material, are observed.

9 Claims, 17 Drawing Figures

Fig. 6(A) IN CASE OF X>0
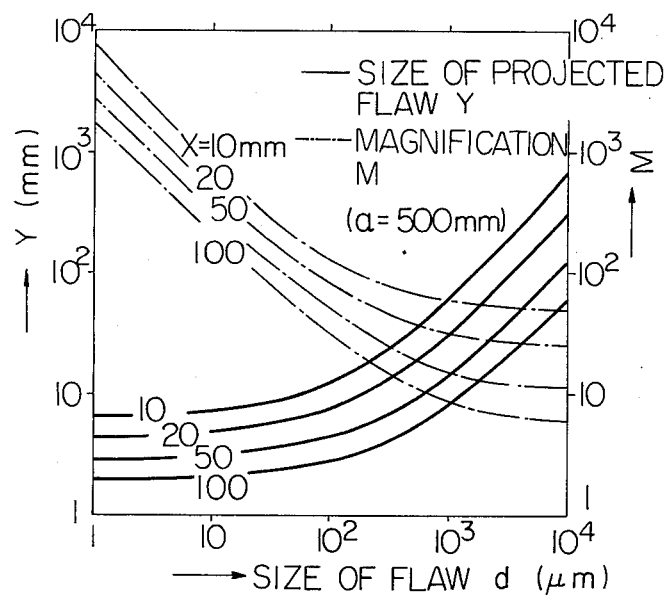
Fig. 6(B) IN CASE OF X<0
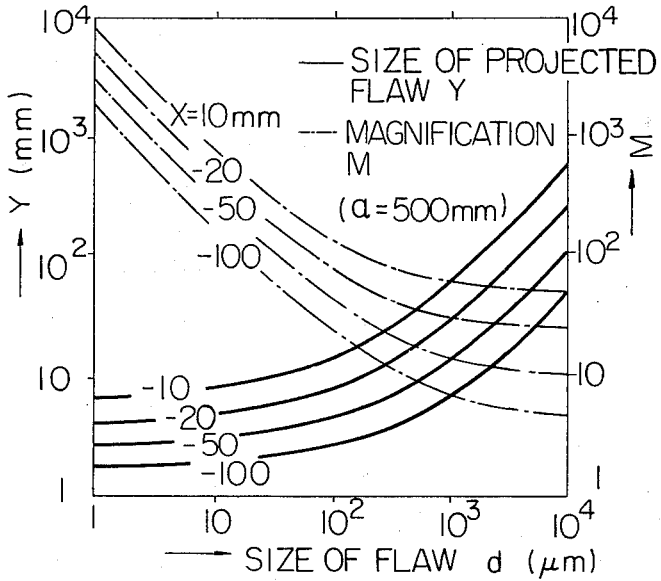

OBLIQUE ILLUMINATION TYPE

NORMAL ILLUMINATION TYPE

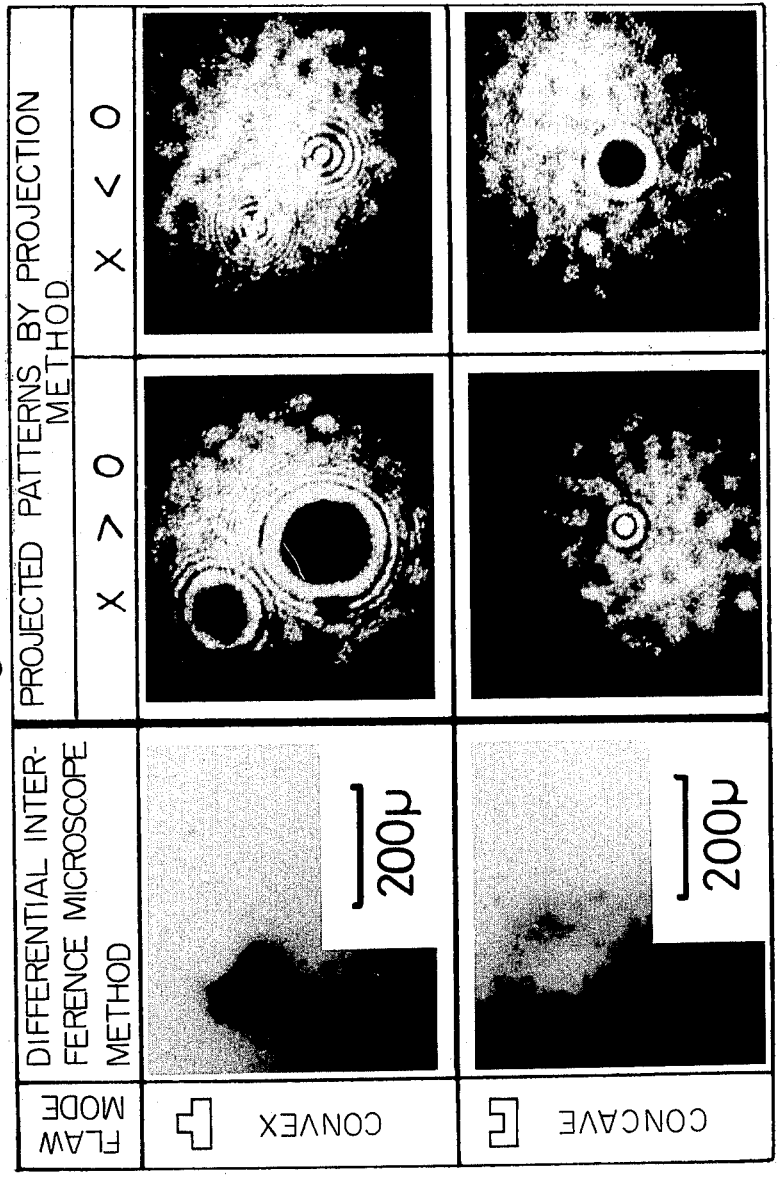

METHOD FOR INSPECTING FLAWS OF MATERIAL

The present invention relates generally to a method for inspecting surface conditions or internal conditions of diverse materials, and more particularly relates to a method for inspecting flaws of materials through employment of a coherent and spherical wave of light, such as Laser light.

In the most typical conventional method for inspecting or observing surface conditions or internal conditions of diverse materials, a known microscopic device has been used. Quite recently another method has been proposed in which a coherent and flat wave of light, such as Laser light, is irradiated or guided to impinge upon a surface of material to be inspected and, then, a Fourier conversion pattern of the material surface is observed ,so that an averaged roughness of said material surface is measured. However, in the case of said recent method, if a given region of the material surface should be observed, concave or convex flaws of the given region of the material surface are all averaged. As a result, it is quite impossible to simultaneously observe both distribution of swells existing on the surface of the material and micro convex or concave flaws of the material.

A further conventional method has also been proposed, in which a spherical wave of Laser light is merely used as a kind of inspecting probe. That is to say, the pencil of the Laser light is converged into a spot of light having a diameter of several micrometers, and the spot of light is scanned across every point of a given surface of a substrate. Then, in response to change in intensity of the Laser light as it is reflected from each point, a diagram showing the distribution of flaws on the substrate surface is acquired. However, in this method it is required that the spot of light of the Laser light impinges upon the substrate surface quite frequently in order to scan all of the points on the substrate surface. For example, in the case of a substrate of one hundred square-millimeters, the spot of light must impinge upon the substrate surface between $10^6$ and $10^8$ times. Therefore, as is obvious from this fact, a highly accurate high speed inspection is difficult.

In order to obviate the drawbacks encountered in the above-mentioned conventional methods, the object of the present invention is to provide a method for simultaneously carrying out a direct and two-dimensional observation and inspection of micro surface conditions, such as micro concave and convex flaws together with macro surface conditions, such as surface swells, of materials or goods. The material or goods may be ceramic material, glass material, optical crystals, magnetic drum or magnetic disc. In the method of the present invention, a coherent and spherical wave of light is employed for illuminating an extensive region of the material or goods.

In accordance with one aspect of the present invention, a method for inspecting flaws of material through employment of a coherent and spherical wave of light comprises the steps of:

guiding the coherent and spherical wave of light so as to impinge upon an extensive region of the material to be inspected;

receiving projections of said region on an inspection screen located at a place which is a predetermined distance from said material, and;

projecting a Fresnel diffraction pattern of said region onto said inspection screen so that said Fresnel diffraction pattern of said region is observed whereby said region is inspected with regard to whether it includes flaws or not.

In accordance with another aspect of the present invention, a method for inspecting flaws existing on a surface of a light reflectable material comprises:

illuminating a selected extensive region on the surface of the light reflectable material by a spherically waved Laser light, and;

subsequently projecting said Laser light reflected from said surface onto a screen located at a position which is a predetermined distance from said surface of said material so that Fresnel diffraction of said flaws is projected onto said screen thereby enabling observation of the shape of said projected Fresnel diffraction pattern on said screen as a two-dimensional pattern.

In accordance with a further aspect of the present invention, a method for inspecting flaws existing in and on a transparent material comprises:

illuminating an extensive selected region in and on the transparent material containing the flaws by a spherically waved Laser light, and;

subsequently projecting said Laser light which passed through said transparent material onto a screen located at a position which is a predetermined distance from said transparent material so that Fresnel diffraction of said flaws is projected onto said screen thereby enabling observation of the shape of said projected Fresnel diffraction on said screen as a two-dimensional diffraction pattern of said flaws.

Each aspect of the present invention will now be further described with reference to the accompanying drawings in which:

FIG. 1 is a schematic and diagramatic view of an embodiment of an optical inspecting system for carrying out a method for inspecting flaws of material according to the present invention;

FIGS. 2(A), (B) and (C) are diagramatic and sectional views of examples of materials which could be inspected by employing a method according to the present invention, respectively;

FIGS. 3(A), (B), (C) and (D) are diagramatic and plan views of projected patterns of various flaw modes which are observed by a method according to the present invention, respectively;

Figure 7A:
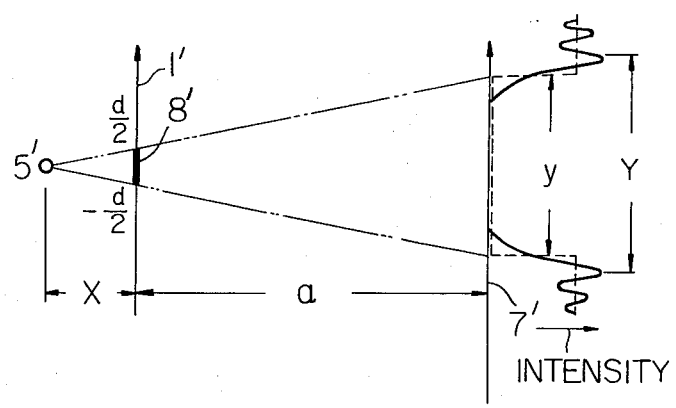
Figure 8A:
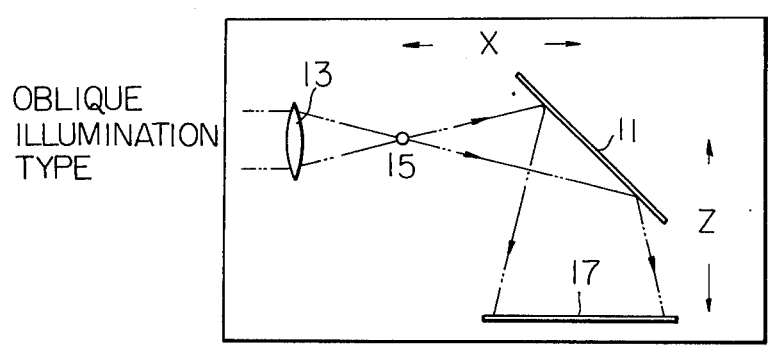

FIGS. 6(A) and (B) are graphs which show the change in actual sizes of projected patterns, and the rate of magnification with respect to change in the size of flaws, respectively;

FIGS. 7(A) and (B) are two other embodiments of optical inspecting systems for carrying out a method of the present invention, which systems employ divergent and convergent spherical waves of lights for illuminating transparent materials, respectively;

FIGS. 8(A) and (B) are two further embodiments of optical inspecting systems for carrying out a method of the present invention, in which systems materials to be inspected are positioned so as to be on a slant and so as to be perpendicular with respect to the axis of the lens system, respectively;

FIG. 9 is composed of experimental photographs which show a comparison between the conventional differential interference method and a method of the present invention.

Figure 1:
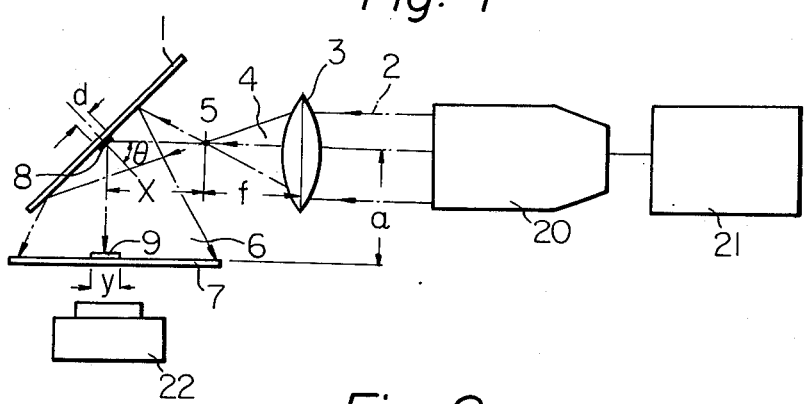

FIG. 1 shows an embodiment of an inspecting system for carrying out a method, according to the present invention, for inspecting surface conditions of opaque and light-reflectable materials such as a ceramic substrate used for a hybrid integrated circuit (HIC). In this figure, system components are referred to by the following reference numerals and symbols. 1 is an opaque and light-reflectable material to be inspected; 2 is a coherent and flat wave of light, such as Laser light; 3 is a convex lens; 4 is a coherent and spherical wave of light converted by the lens 3 from the flat wave of light 2; 5 is the focal point of the lens 3; 6 is a light reflected from the surface of the material 1; 7 is an inspection screen; 8 is a micro flaw, such as for example, concave or convex, existing on the surface of the material; 9 is the projected Fresnel diffraction pattern of the flaw 8; $f$ is the focal distance of the lens 3; X is a distance between the focal point 5 and the flaw 8, and is referred to as "illuminating distance" in this specification; $a$ is a distance between the flaw 8 and the pattern 9; $d$ is a size of the flaw 8; $y$ is a size of the pattern 9; $\theta$ is an angle made between the optical axis of the lens 3 and the perpendicular line on the surface of the material 1; 20 is a system for diverging the pencil of the Laser light; 21 is a He-Ne Laser, and; 22 is a video-camera.

Referring to FIG. 1, said flat wave of Laser light 2 radiating from the diverging system 20 is converted by the convex lens 3 into the spherical wave of Laser light 4 which converges into the focal point 5. Passing through the focal point 5, said spherical wave of light 4 diverges and is guided or irradiated to impinge upon an extensive region on the surface of the material 1. The material is positioned so as to be on a slant at an angle $\theta$, for example 45°, with respect to the optical axis of the lens 3, and thus the light 6 reflected from said region on the surface of the material 1 is projected onto the inspection screen 7 which is located at a position which is a predetermined distance from the material 1. Thus, the Fresnel diffraction pattern 9 of the flaw 8 existing on the surface of the material 1 is projected onto the inspection screen 7, whereby the flaw 8 can be observed in a two-dimensional pattern at a magnified scale.

The inspection screen 7 may take the form of, for example, a frosted glass. In this case, the pattern 9, may be monitored by means of a video-camera 22 disposed behind the inspection screen and a video-monitor.

Figure 2:
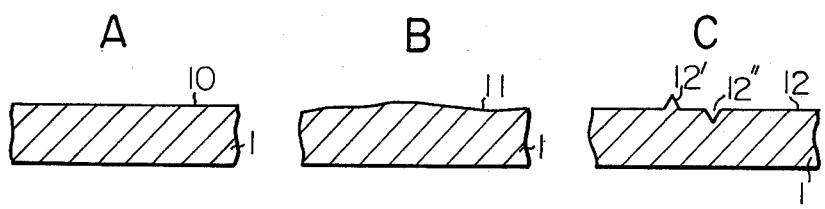

FIGS. 2(A), 2(B) and 2(C) are sectional views showing examples of the surface condition of a material. FIG. 2(A) shows a material having a completely flat surface 10. FIG. 2(B) shows a material having a surface 11 which swells at a large pitch. FIG. 2(C) shows a material having a surface 12 which includes micro convex 12' and concave 12" flaws.

Figure 3:
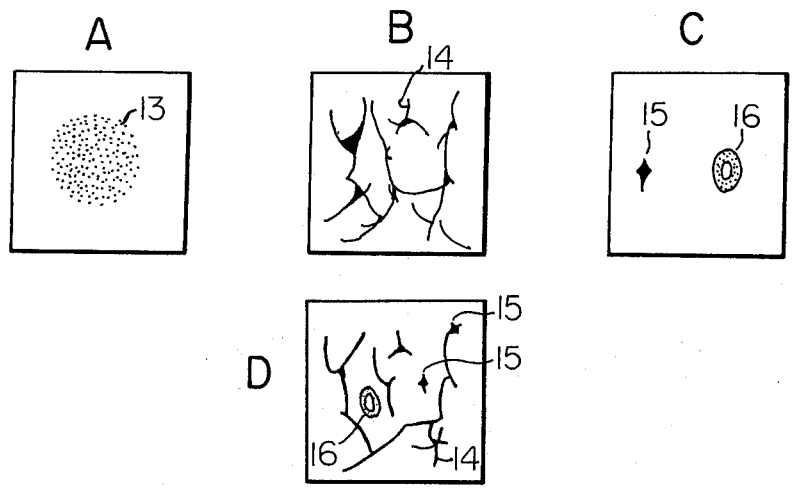

FIGS. 3(A), 3(B), 3(C) and 3(D) are diagramatic views of the Fresnel diffraction pattern, and show the distribution, on the inspection screen, of the light reflected from the material surface. FIG. 3(A) shows the distribution of the light reflected from the completely flat surface 10 shown in FIG. 2(A). FIG. 3(B) shows the distribution of the light reflected from the swelling surface 11 shown in FIG. 2(B). FIG. 3(C) shows the distribution of the light reflected from the surface 12, shown in FIG. 2(C), including the micro convex 12' and concave 12" flaws, wherein parts 15 and 16 correspond to the convex 12' and concave 12" flaws, respectively. FIG. 3(D) shows the distribution of the light reflected from a surface which swells at a large pitch and includes micro convex 12' and concave 12" flaws such as shown in FIG. 2(C). It should be noted that, in FIGS. 3(A) through 3(D), the smeared out parts in block correspond to the parts having strong luminosity.

In the method according to the present invention, a coherent and spherical wave of light is employed, and the condition of the material, that is, the existence of flaws, can be inspected by way of observing the two-dimensional Fresnel diffraction pattern projected onto the inspection screen 7.

Figure 4:
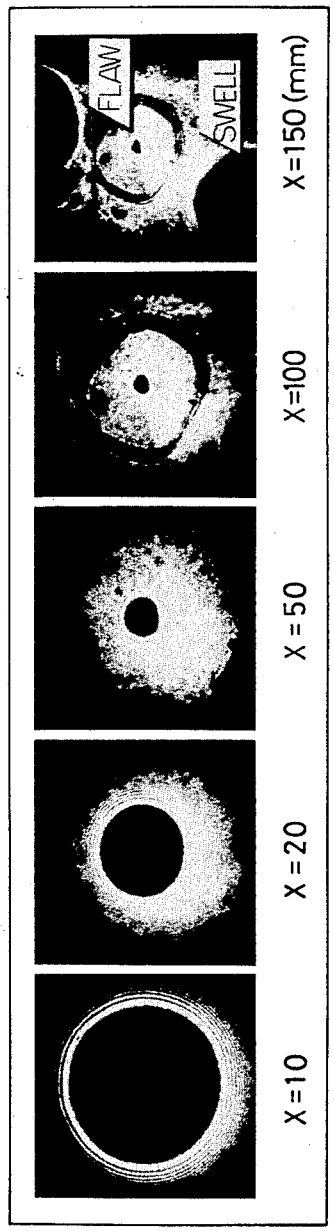
FIG. 4 is composed of photographs which show that the Fresnel pattern of a flaw is magnified by changing the illuminating distance X.

It is one advantage of the present invention that the magnification of flaws, that is, the size of the projected pattern of the flaws can be changed, although the shape of said projected pattern is different from, but appropriate to, the original shape of the flaws. Therefore, as shown in FIG. 1, when the focal distance $f$ of the lens 3 is changed, the divergency of the spherical wave of light 4 varies, while when the illuminating distance X between the material 1 and the focal point 5 is changed, the size of the region of the material 1, on which the light 4 is irradiated, varies. Thus, it is possible to not only freely select the region to be inspected but also to change the size thereof, and to magnify or reduce the size of the projected pattern 9 of flaws. FIG. 4 shows the Fresnel diffraction patterns obtained in the cases where the illuminating distance X equals 10, 20, 50, 100 and 150 (mm), respectively. As will be seen from this figure, in the case of X = 10 (mm), the projected patterns of flaws are magnified in size and, thus, the pattern of a micro flaw only can be observed. While in the case of X = 150 (mm), the projected patterns of flaws are reduced in size and, thus, a micro flaw and surface swell, which is a macro flaw, can be observed simultaneously.

It is a very important advantage of the present invention that the micro flaw and macro flaw can be observed simultaneously, as shown in FIG. 4 in the case of X = 150 (mm). This is based upon the fact that the smaller a flaw is in size, the more the projected pattern of the flaw is magnified in size, that is to say, the magnification of a micro flaw is larger, while the magnification of a macro flaw is smaller.

Figure 5:
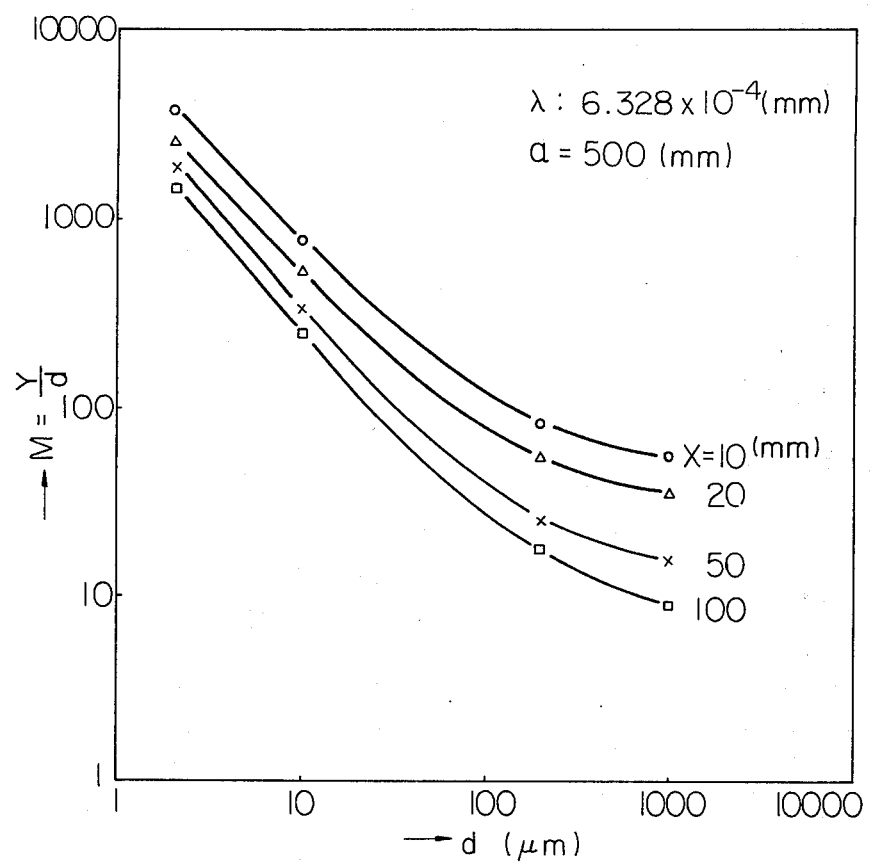
FIG. 5 is an experimental graph which shows the relationship between the size of flaws and the rate of magnification.

The diagrams of FIG. 5 show experimental data of the magnifications M of the flaw 8 with respect to the size $d$ of the flaw, when the illuminating distance X is changed. In FIG. 5, the abscissa shows the size $d$ ($\mu$: micrometer) of the flaw 8 in logarithmic scale, and the ordinate shows the magnification M (non-dimensions) in logarithmic scale.

The magnification M of a flaw is theoretically the ratio of the size Y of the Fresnel diffraction pattern of the flaw to the size $d$ of the flaw, and is defined as $$M = Y/d$$

The size Y of the Fresnel pattern of a flaw can be expressed approximately as follows:

$$Y = 2.434 \sqrt{\frac{\lambda}{2} \cdot \frac{X+a}{|x|} + \frac{X+a}{|x|} \cdot d} \quad (1)$$

wherein: $\lambda$ is the wave length of the Laser light, in the case of an He-Ne Laser, $\lambda = 6.328 \times 10^{-4}$ (mm); when the light is divergent, X is defined as X > 0, and when the light is convergent, X is defined as X < 0.

In the formula (1), it will be understood that the first term of the right member is the component based upon the Fresnel diffraction and is constant with respect to $d$, while the second term of the right member is the size of the image of a flaw obtained by the geometrical optics method.

Therefore,

Therefore, $$M = 2.434 \cdot \frac{1}{d} \sqrt{\frac{\lambda}{2} \cdot \frac{X+a}{|X|} + \frac{X+a}{|X|}} \quad (2)$$

As will be understood from the formula (2), the smaller $d$ is, the larger the first term of the right member becomes and, thus, the larger M becomes.

Figure 7B:
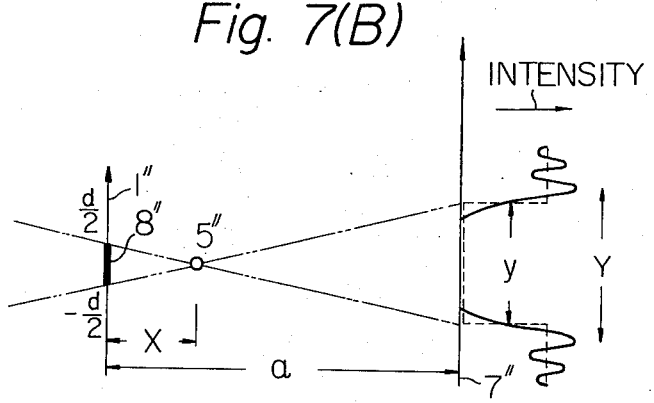

The Y and M calculated by the formula (1) and (2), respectively, in the case where $\lambda = 6.328 \times 10^{-4}$ (mm), $a = 500$ (mm), and X = 10, 20, 50 and 100 (mm), are shown in the diagrams of FIGS. 6(A) and 6(B). The diagrams of FIG. 6(A) correspond to the divergent spherical wave of light such as shown in FIG. 7(A), and in this case, X is defined as X > 0. While the diagrams of FIG. 6(B) correspond to the convergent spherical wave of light as shown in FIG. 7(B), and, in this case, X is defined as x < 0. In these FIGS. 6(A) and 6(B), both the abscissa and ordinate have logarithmic scales. Further, y shown in FIGS. 7(A) and 7(B) indicates the size of the image of a flaw obtained by the geometrical optics method and corresponds to the second term of the right member in the formula (1).

As will be understood from the above described experimental and theoretical results, since the smaller the size $d$ of the flaw is, the larger the magnification M of the flaw is, in a case where an extensive region is inspected, micro concave or convex flaws and macro flaws such as surface swells can be observed simultaneously. Further, by changing the illuminating distance X, it is possible to vary the magnification M of each flaw so that individual flaws can be observed distinct from each other.

The foregoing description with reference to FIG. 1 through FIGS. 6(A) and 6(B) is mainly directed to an embodiment of an inspection method for flaws of an opaque material and a light reflexible material, such as a ceramic substrate used for a hybrid integrated circuit. In the case of a transparent material, a spherically waved light, which is passed through the transparent material to be inspected, will be projected on an inspection screen as is shown in FIG. 7(A) and FIG. 7(B).

Also, it should be noted that the spherically waved light which impinges upon materials to be inspected, may take either the form of a divergent wave of light or a convergent wave of light.

FIG. 7(A) shows an embodiment of an inspecting system for carrying out a method in which a divergent and spherical wave of light is irradiated on a transparent material to be inspected.

In FIG. 7(A), a focal point 5' of the lens system (not shown) forms a point source from which a spherical wave of light diverges toward a transparent material 1' which includes a flaw 8'. The spherical wave of light passes through the material 1', and subsequently it is projected on a screen 7'. That is to say, the point source 5' is located at the leftward most end of the inspecting system of FIG. 7. In this inspecting system, the value of the illuminating distance designated by X is defined as positive.

FIG. 7(B) shows an embodiment of an inspecting system for carrying out another method in which a convergent and spherical wave of light is irradiated on a transparent material to be inspected.

In FIG. 7(B), it should be noted that the spherical wave of light which impinges upon the material 1'', passes through the material 1'' and subsequently converges on a focal point 5'' of the convex lens system (not shown). The spherical wave of light having converged on the converging point 5'', subsequently diverges, and is projected on a screen 7'' so as to produce a projection of a flaw 8'' of the material 1'' on the screen 7''. It should be appreciated that in the inspecting system of FIG. 7(B), the converging point 5'' is located between the material 1'' and the screen 7''. That is to say, in the system of FIG. 7(B), the value of the illuminating distance X is defined as negative. In both FIGS. 7(A) and 7(B), the intensity of each diffraction pattern of flaws 8' and 8'' are diagramatically represented at the right side of each screen 7' or 7''.

Figure 8B:
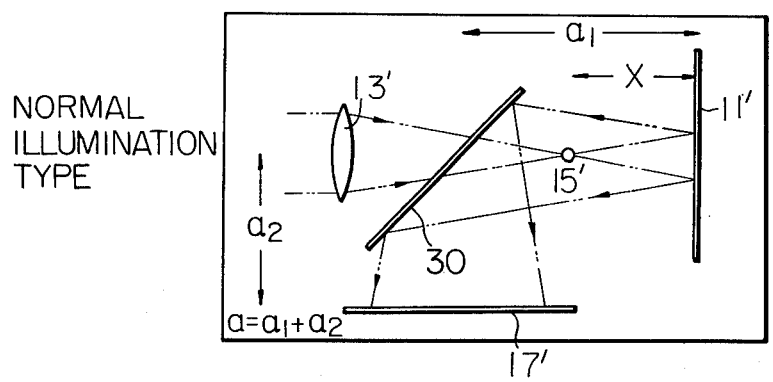

FIGS. 8(A) and 8(B) each show a different embodiment of inspecting systems which illustrate two further different methods for illuminating materials to be inspected by coherent and spherical waves of light.

From FIG. 8(A), it will be understood that the inspecting system, is formed so that the spherical wave of light from a focal point 15 of a convex lens 13, obliquely impinges upon a material 11 to be inspected, and then the wave of light is reflected from the surface of the material 11 so that it is projected on a screen 17 located at the lower part of the inspecting system of FIG. 8(A). That is, the material 11 to be inspected is positioned so as to be on a slant with respect to the axis of the convex lens 13.

From FIG. 8(B), it will be understood that the inspecting system is formed so that a material 11' to be inspected, is positioned so as to be perpendicular to the axis of a convex lens 13'. Therefore, the coherent and spherical wave of light from a point source 15' normally impinges upon the surface of the material 11'. In this system of FIG. 8(B), it should be noted that in order to enable the projection of the wave of light reflected from the material 11' on a screen 17', a half-mirror or semitransparent mirror 30 is located in the light passageway between the material 11' and the screen 17'.

FIG. 9 shows photographs which enable comparison between the conventional differential interference microscope method and the projection method of the present invention. In FIG. 9, the upper line of photographs shows a case where flaws of the material are of convex form, while the lower line shows a case where flaws of the material are of concave form. From the photographs, it will be understood that in the projection method of the present invention, the projected Fresnel pattern employing a divergent spherical wave of light (X > 0) and the projected Fresnel pattern employing a convergent spherical wave of light are different in that black and white images are completely reversed between both said patterns. Also, it should be appreciated that in the conventional differential interference microscope method, merely a single flaw can be observed, while in the projection method of the present invention, diffraction patterns of two flaws can clearly be observed on a common inspection screen. As a result, the projection method of the present invention is very effective for inspecting an extensive region of material.

From the foregoing description of the method of the present invention, it will be understood that the employment of a coherent and spherical wave of light for illuminating a material to be inspected, according to the present invention, enables simultaneous inspection or observation of micro convex and concave flaws together with macro flaws, such as swells, which exist together in or on the material, since such micro flaws are caught in enlarged patterns, and such macro flaws are caught in reduced patterns on a common inspection screen. Therefore, it should be appreciated that the projection method of the present invention is quite advantageous compared with the conventional inspecting methods employing a microscope, or a Fourier conversion pattern of a flat wave of light.

What is claimed is:

1. A method for inspecting flaws in material, comprising the steps of:
   a. directing a parallel beam generated from a source of a coherent wave of light through a spherical lens;
   b. forming a cone-shaped coherent spherical wave of light by focusing said parallel beam to a focal point of said spherical lens;
   c. positioning said material in a manner to provide intersection of said cone-shaped coherent spherical wave of light and a region of said material at a predetermined distance from said focal point, said region of said material on which said cone-shaped coherent spherical wave of light impinges being substantially larger than the size of said flaws to be inspected;
   d. positioning an inspection screen at a predetermined distance from said material to intersect light reflected from said region in order that a Fresnel diffraction pattern of microflaws to be inspected becomes an observable size; and,
   e. observing said inspection screen with regard to whether or not said distribution of said light reflected from said region includes a Fresnel diffraction pattern of said microflaws thereby enabling detection of said microflaws within said region of said material to be inspected.

2. A method as claimed in claim 1, wherein said coherent spherical wave of light is a spherical wave of Laser light.

3. A method as claimed in claim 1, wherein said coherent spherical wave of light takes the form of a divergent pencil of light when said coherent spherical wave of light illuminates said material.

4. A method as claimed in claim 3, further comprising adjusting the distance between said material and the source of said divergent pencil of light thereby enabling adjustment of magnification in said projected Fresnel diffraction pattern of said flaws.

5. A method as claimed in claim 1, wherein said coherent spherical wave of light takes the form of a convergent pencil of light when said coherent spherical wave of light illuminates said material.

6. A method as claimed in claim 5, further comprising adjusting the distance between said material and the point toward which said convergent pencil of light is gathered, thereby enabling adjustment of magnification in said projected Fresnel diffraction pattern of said flaws.

7. A method as claimed in claim 1, wherein said material is positioned to be on a slant with respect to the direction of guiding of said coherent spherical wave of light.

8. A method as claimed in claim 1, wherein said material is positioned to be perpendicular to the direction of guidance of said coherent and spherical wave of light, and wherein a semitransparent mirror is disposed to face said material with an angularity whereby after said coherent and spherical wave of light is reflected from said material, said wave of light is reflected by said mirror toward said inspection screen.

9. A method for inspecting flaws existing in and on a transparent material comprising:
   a. directiing a parallel beam generated from a source of coherent wave of light through a spherical lens;
   b. forming a cone-shaped coherent spherical wave of light by focusing said parallel beam to a focal point of said spherical lens;
   c. positioning said transparent material in a manner to provide intersection of said cone-shaped coherent spherical wave of light and a region of said material at a predetermined distance from said focal point, said region of said transparent material on which the said cone-shaped coherent spherical wave of light impinges being substantially larger than the size of said flaws to be inspected;
   d. positioning an inspection screen at a predetermined distance from said transparent material to intersect light passing through said transparent material in order that a Fresnel diffraction pattern becomes an observable size; and
   e. observing said inspection screen with regard to whether or not said distribution of said light passing through said region includes a Fresnel diffraction pattern of said flaws thereby enabling observation of the shape of said projected Fresnel diffraction pattern on said screen as a two-dimensional diffraction pattern of said flaws.

* * * * *